United States Patent

Tan et al.

[11] Patent Number: 6,130,339
[45] Date of Patent: Oct. 10, 2000

[54] ELECTRO-ACTIVE MONOMERS COMPRISED OF ANILINE-THIOPHENE UNITS

[75] Inventors: Loon-Seng Tan, Centerville; Devdatt S. Nagvekar; Balasubramanian Sankaran, both of Dayton, all of Ohio

[73] Assignee: The United States of America as represented by the Secretary of the Air Force, Washington, D.C.

[21] Appl. No.: 09/323,647

[22] Filed: Jun. 1, 1999

[51] Int. Cl.[7] .................... C07D 495/02; C07D 409/04
[52] U.S. Cl. .................... 549/50; 549/59; 549/60
[58] Field of Search .................... 549/50, 59, 60

[56] References Cited

U.S. PATENT DOCUMENTS 4,940,517  7/1990  Wei .
5,527,434  6/1996  Hamnett et al. .

OTHER PUBLICATIONS

D. Nagvekar, B. Sankaran, L–S Tan, Synthesis and Electrochemical Characterization of Electro–Active Monomers Containing Directly Bonded Aniline–Thiophene, Aniline–bithiophene and Anilne–Ethylenedioxythiophene Structures, Polymer Preprints, vol. 39, No. 2, Aug. 1998, pp. 548–549, published Jul. 16, 1998.

S.C. Ng, L.G. Xu, H.S.O. Chan, A novel conductive polymer: poly[4–(2-thienyl)benzenamine], J. Mater. Sci. Letters, 16(1997), 1738–1740. (no month given.).

J. Guay, M. Leclerc, L.H. Dao, Conducting polymer derived from 4–aminobiphenyl, J. Electroanal. Chem., 251(1988), 31–39. (no month given.).

D.R. McKean, G. Parrinello, A.F. Renaldo, J.K. Stille, Synthesis of Functionalized Styrenes via Palladium–Catalyzed Coupling of Aryl Bromides with Vinyl Tin Reagents, J. Org. Chem., 1987, 52, 422–424. (no month given.).

S.C. Ng, L. Xu, Poly[4–(2–heteroaryl)benzenamines]:Novel Electrically Conducting Alternating Copolymers of Aniline and Chalcophenes, Adv. Mater. 1998, 10, No. 18, pp 1525–1529. (no month given.).

*Primary Examiner*—Shailendra Kumar
*Attorney, Agent, or Firm*—Charles E. Bricker; Thomas L. Kundert

[57] ABSTRACT

Provided are novel, electropolymerizable monomers of the formulae:

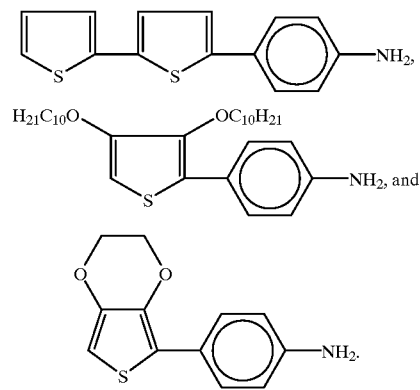

3 Claims, No Drawings

ELECTRO-ACTIVE MONOMERS COMPRISED OF ANILINE-THIOPHENE UNITS

RIGHTS OF THE GOVERNMENT

The invention described herein may be manufactured and used by or for the Government of the United States for all governmental purposes without the payment of any royalty.

BACKGROUND OF THE INVENTION

The present invention relates to novel aniline-thiophene monomers.

The electrical conductivity ($\sigma$) of most organic materials at room temperature is quite small ($\sigma < 10^{-10}$ ohm$^{-1}$cm$^{-1}$). Over the last two decades, the synthesis of organic molecules with electrical properties approaching those of metals have been the focus of considerable attention. Because organic polymers generally have elasticity, strength and plasticity, they offer significant advantages over non-polymeric materials in the manufacture of electronic materials. Macromolecular substances can now be tailored to perform as semiconductors or even as true organic metals.

The field of organic metals is dominated by two types of molecular structures: linearly conjugated π-systems and charge-transfer complexes which form stacks of π-systems in the solid state. In the former systems, electrons move rapidly along a partially oxidized or reduced molecular chain. Examples of linear π-conjugated systems are polypyroles, polythiophenes, polyanilines, polyacetylenes and polyarylenes. In charge-transfer complexes, electrons move along a partially oxidized or reduced stack of molecules. In either case, the electrical, optical and magnetic properties are a complex function of the solid state structure, and efforts have been made to prepare and study model compounds for these systems, primarily in solution.

Among the families of organic synthetic metals, poly(thiophene) (PTh) and polyaniline (PANI) and their derivatives may be the most extensively prepared and studied systems in recent years. While the former, as a whole, has generally higher p-doped conductivity, the latter enjoys a better temporal stability with respect to conductive properties at ambient conditions.

We have synthesized new electro-active monomers, as well as polymers therefrom, comprising thiophene and aniline units linked by a direct C—C bond.

Accordingly, it is an object of the present invention to provide new electro-active monomers comprising thiophene and aniline units linked by a direct C—C bond.

Other objects, aspects and advantages of the present invention will be apparent to those skilled in the art from a reading of the following detailed disclosure of the invention.

SUMMARY OF THE INVENTION

In accordance with the present invention there are provided novel, electropolymerizable monomers of the formulae:

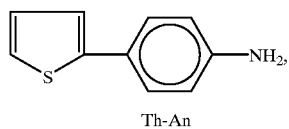

Th-An

-continued

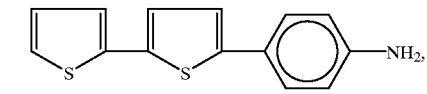

Th-Th-An

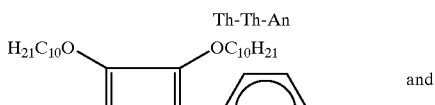

C$_{10}$OThC$_{10}$O-An

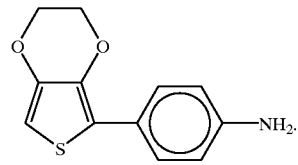

EDOT-An

These monomers are synthesized by the palladium-catalyzed coupling reaction of 1-halo-4-nitrobenzene with the corresponding 2-(tributylstannyl)thiophene, followed by reduction of the nitro intermediates, as shown in the examples which follow. The coupling reaction works well in dioxane or toluene at reflux with tetrakis(triphenylphosphine)palladium(0), Pd(PPh$_3$)$_4$.

These monomers are preferably electrochemically polymerized. Electrochemical polymerization of the above-described monomers can be carried out according to the methods generally employed for electrochemical polymerization of thiophene, pyrrole, and the like. The electrochemical copolymerization is carried out by cyclic voltammetry, by subjecting a mixture of monomer, solvent and electrolyte to one of the following conditions: (a) setting the potentiostat at a constant electrical potential where the monomer is optimally oxidized; (b) setting the potentiostat at a constant current value; or (c) repeated scanning between the redox potentials of the monomers. Typically, all three conditions are tested for a new monomer in order to select one as the optimal condition for achieving electropolymerized polymer films with the required stability and thickness. If the oxidation-reduction cycle can be repeated several times and the polymer film deposited on the electrode exhibits reproducible cyclic voltammetric (current-voltage) characteristics, it is then deemed to be electrochemically stable and well-behaved.

The solvents which can be used in the present invention may be either aqueous or nonaqueous, although a solution of the aforesaid electrolyte in a nonaqueous organic solvent is preferred. The organic solvents used herein are preferably aprotic and have high dielectric constants. For example, ethers, ketones, nitrites, amines, amides, sulfur compounds, phosphoric ester compounds, phosphorous ester compounds, boric ester compounds, chlorinated hydrocarbons, esters, carbonates, nitro compounds and the like can be employed. Of these, ethers, ketones, nitrites, phosphoric ester compounds, phosphorous ester compounds, boric ester compounds, chlorinated hydrocarbons and carbonates are preferred. Specific examples of suitable solvents include tetrahydrofuran, 2-methyltetrahydrofuran, 1,4-dioxane, acetonitrile, propionitrile, 4-methyl-2-pentanone, butyronitrile, valeronitrile, benzonitrile, 1,2-dichloroethane, gammabutyrolactone, valerolactone, dimethoxyethane, methylformate, propylene carbonate, ethylene carbonate, dimethylformamide, dimethyl sulfoxide, ethyl phosphate, methyl phosphate, ethyl phosphite, methyl phosphite, 3-methylsulfolane, etc. Among these, nitriles and carbonates are especially preferred in order to increase the response speed. These organic solvents may be used alone or in combination.

Specific examples of electrolyte which can be used in the present invention include tetraphenylarsonium chloride, tetraphenylphosphonium chloride, tetra(n-butyl)ammonium bromide, lithium bromide, tetra(n-butyl)ammonium hexafluorophosphate, and tetra(n-butyl)ammonium perchlorate (TBAP). These examples are merely illustrative and not limiting.

Within the context of the implementation of the process in accordance with the invention, the electrochemical reactions are advantageously carried out at the surface of an electrode. By measuring the current delivered during the reaction, the electrode effectively makes it possible to monitor the progress of the polymerization reaction (for example the thickness of the polymer formed) or the progress of subsequent reactions carried out on the copolymer.

The resulting polymers have repeating units of the formula:

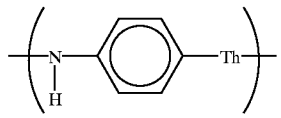

wherein Th is

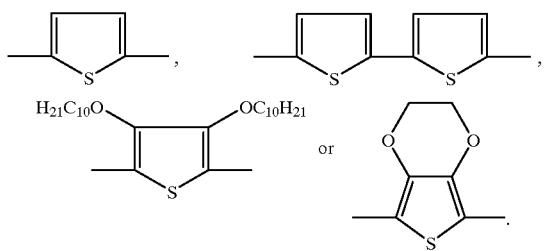

The following examples illustrate the invention:

EXAMPLE 1

2-(Tributylstannyl)-2,2'-bithiophene n-Butyllithium (22.0 mL, 55.0 mmol, 2.5 M solution in hexane) was added dropwise at −78° C. to a solution of 2,2'-bithiophene (9.44 g, 56.78 mmol) in anhydrous THF (600 mL) under nitrogen. The solution was stirred for 1 h and warmed to −40° C. Tributylstannyl chloride (17.90 g, 55.00 mmol) was added and the entire solution was finally allowed to warm to room temperature. At room temperature the mixture was filtered using Celite and the solvent was stripped. The organo-tin compound was vacuum dried to give 2-(tributylstannyl)-2,2'-bithiophene, obtained as a dark yellow liquid, yield=99%. MS(EI) m/z (rel int): 456 [(M)$^+$, 18%] and 399 [(M)$^+$—C$_4$H$_9$, 76%].

EXAMPLE 2

2-(Tributylstannyl)-3,4-(ethylenedioxy)thiophene n-Butyllithium (77 mL, 192.5 mmol, 2.5 M solution in hexane) was added dropwise at −78° C. to a solution of 3,4-(ethylenedioxy)thiophene (25 g, 175.9 mmol) in anhydrous THF (100 mL) under nitrogen. The solution was stirred for 1 h and warmed to −40° C. Tributylstannyl chloride (85.89 g, 263.9 mmol) was added and the entire solution was finally allowed to warm to room temperature. At room temperature the mixture was filtered using Celite and the solvent was stripped. The organo-tin compound was vacuum dried to give 2-(tributylstannyl)-3,4-(ethylenedioxy)thiophene, obtained as a dark yellow liquid, yield=98%. MS(EI) m/z (rel int): 375 [(M)$^+$—C$_4$H$_8$, 100%] and 319[(M)$^+$—C$_8$H$_{16}$, 18%].

EXAMPLE 3

2-(tributylstannyl)-3,4-didecyloxythiophene n-Butyllithium (1.8 mL, 4.5 mmol, 2.5 M solution in hexane) was added dropwise at −78° C. to a solution of 3,4-didecyloxythiophene (1.86 g, 4.69 mmol) in anhydrous THF (200 mL) under nitrogen. The solution was stirred for 1 h and warmed to −40° C. Tributylstannyl chloride (1.47 g, 4.52 mmol) was added and the entire solution was finally allowed to warm to room temperature. At room temperature the mixture was filtered using Celite and the solvent was stripped. The organo-tin compound was vacuum dried to give 2-(tributylstannyl)-3,4-didecyloxythiophene, obtained as a light yellow liquid, yield=99%. MS(EI) m/z (rel int): 629 [(M)$^+$—C$_4$H$_9$, 22%], 396 [(M$^+$—C$_{12}$H$_{27}$Sn), 8.5%], 256 [(M$^+$—C$_{22}$H$_{47}$Sn), 3%] and 116 [(M$^+$—C$_{32}$H$_{67}$Sn), 43%].

EXAMPLE 4

1-(2-Thienyl)-4-nitrobenzene

To a refluxing solution of 1-bromo-4-nitrobenzene (2.525 g, 12.5 mmol) in toluene (200 mL) was added tetrakis(triphenylphosphine)palladium(0) (78 mg). After 20 min, 2-(tributylstannyl)thiophene (5.2 g, 6.1 mL, 13.9 mmol) was added via a syringe. After complete addition, the mixture was refluxed for a total of 24 to 48 h. After cooling, the mixture was filtered and then subjected to rotary evaporation to give a solid. Filtration using hot hexane gave pure 1-(2-theinyl)-4-nitrobenzene, yield=94%, mp=124–126° C. IR (KBr, in cm$^{-1}$) 3105, 1593, 1508, 1336, 1108 and 850. $^1$H NMR (CDCl$_3$; δ in ppm): 7.143 (dd, J=5.7 and 3.9 Hz, 1H), 7.449 (m, 2H), 7.722 (d, J=9.8 Hz, 2H) and 8.217 (d, J=9.8 Hz, 2H). $^{13}$C NMR (CDCl$_3$; δ in ppm): 124.34, 125.67, 125.96, 127.65, 128.66, 140.50, 141.51 and 146.52. MS(EI) m/z (rel int): 205 [(M)$^+$, 100%], 175 [(M$^+$—NO), 42%], 158 [(M$^+$—HNO$_2$), 23%], 147 [(M$^+$—CO, NO), 24%] and 115 [(M$^+$—CNO$_2$S), 93%]. Anal. Calcd for C$_{10}$H$_7$NO$_2$S: C, 58.52%; H, 3.44%; N, 6.82%; S, 15.62%. Found: C, 58.48%; H 3.54%; N 6.61%; S 15.23%.

EXAMPLE 5

1-(2-Thienyl)-4-aminobenzene

A solution of 1-(2-thienyl)-4-nitrobenzene (1.65 g, 8.05 mmol) in 95% ethanol (210 mL) containing platinum on sulfide carbon (50 mg) was added hydrazine hydrate (0.5 mL). The mixture was refluxed for 2 hours. After cooling, the mixture was filtered and the solvent was evaporated to give a solid. Addition of hexane followed by filtration gave pure 1-(2-thienyl)-4-aminobenzene, yield=98%, 70–72° C. IR (KBr, in cm$^{-1}$) 3440, 3344, 3098, 1620, 1500, 1281, 1183 and 813. $^1$H NMR (CDCl$_3$; δ in ppm): 3.978 (brs, 2H), 6.670 (d, J=9.6 Hz, 2H), 7.011 (dd, J=5.6 and 4.4 Hz, 1H), 7.139

(m, 2H) and 7.382 (d, J=9.6 Hz, 2H). $^{13}$C NMR (CDCl$_3$; δ in ppm): 115.07, 120.95, 122.82, 124.40, 126.91, 127.77, 144.77 and 146.46. MS(EI) m/z (rel int): 175 [(M)$^+$, 100%], 143 [(M$^+$—S), 10%] and 130 [(M$^+$—HCS), 57%]. Anal. Calcd for C$_{10}$H$_9$NS: C, 68.53%; H 5.18; N 7.99. Found: C, 68.50; H, 5.21; N, 7.74.

EXAMPLE 6

1-(3,4-Ethylenedioxythien-2-yl)-4-nitrobenzene

To a refluxing solution of 1-bromo-4-nitrobenzene (2.762 g, 13.67 mmol) in toluene (250 mL) was added tetrakis(triphenylphosphine)palladium(0) (75 mg). After 20 min, 2-(tributylstannyl) 3,4-(ethylenedioxy)thiophene (6.05 g, 14.03 mmol) was added via a syringe. After complete addition, the mixture was refluxed for a total of 20 h. After cooling, the mixture was filtered and the solvent was evaporated to afford a solid. Filtration using hot hexane gave 1-(3,4-ethylenedioxythien-2-yl)-4-nitrobenzene, 2.46 g, yield=68%, mp=184–186° C. IR (KBr; in cm$^{-1}$) 3066, 2946, 1592, 1506, 1477, 1338, 1066 and 851. $^1$H NMR (CDCl$_3$; δ in ppm): 4.285 (m, 2H), 4.376 (m, 2H), 6.468 (s, 1H), 7.852 (d, J=9.9 Hz, 2H) and 8.197 (d, J=9.9 Hz, 2H). $^{13}$C NMR (CDCl$_3$; δ in ppm): 64.25, 64.94, 100.93, 115.10, 124.03, 125.61, 139.72, 140.53, 142.43 and 145.37. MS(EI) m/z (rel int): 263 [(M)$^+$, 27%], 233 [(M$^+$—NO), 8%] and 166[(M$^+$—C$_5$H$_5$O$_2$), 9%]. Anal. Calcd for C$_{12}$H$_9$NO$_4$S: C, 54.75; H, 3.45;, N, 5.32; S, 12.18. Found: C, 55.04; H, 2.99; N, 4.05; S, 11.57.

EXAMPLE 7

1-(3,4-Ethylenedioxythien-2-yl)-4-aminobenzene

A solution of 1-(3,4-ethylenedioxythien-2-yl)-4-nitrobenzene (0.663 g, 2.52 mmol) in 95% ethanol (60 mL) containing platinum on sulfide carbon (50 mg) was added hydrazine hydrate (1.0 mL). The mixture was refluxed for 10 hours. After cooling, the mixture was filtered and the solvent was evaporated to give a solid. Addition of hexane followed by filtration gave 1-(3,4-ethylenedioxythien-2-yl)-4-aminobenzene. It was recrystallized from ethanol, 0.39 g, yield=66%, mp=98.5–99° C. IR (KBr; cm$^{-1}$) 3433, 3352, 3032, 2924, 1624, 1520, 1428, 1365, 1288, 1170, 1071, 920 and 833. $^1$H NMR(CDCl$_3$; δ in ppm): 3.604 (br, s, 2H), 4.208 (m, 4H), 6.176 (s, 1H), 6.651 (d, J=9.6 Hz, 2H) and 7.492 (d, J=9.6 Hz, 2H). $^{13}$C NMR(CDCl$_3$; δ in ppm): 64.45, 64.59, 95.61, 115.10, 117.98, 123.60, 127.25, 136.61, 142.09 and 145.20. MS(EI) m/z (rel int): 233 [(M)$^+$, 55%], 177 [(M$^+$—C$_3$H$_4$O), 6.6%], 149 [(M$^+$—C$_4$H$_4$O$_2$, 11%] and 136 [(M$^+$—C$_5$H$_5$O$_2$] 100%]. Anal. Calcd for C$_{12}$H$_{11}$NO$_2$S: C, 61.78; H, 4.75; N, 6.00; S, 13.74. Found: C, 60.82; H. 4.87; N, 5.64; S, 12.86.

EXAMPLE 8

1-(Bithien-2-yl)-4-nitrobenzene

To a refluxing solution of 1-bromo-4-nitrobenzene (8.10 g, 40.01 mmol) in toluene (650 mL) was added tetrakis(triphenylphosphine)palladium(0) (175 mg). After 20 min, 2-(tributylstannyl)bithiophene (20.29 g, 44.56 mmol) was added via a syringe. After complete addition, the mixture was refluxed for a total of 15 h. After cooling, the mixture was filtered and the solvent was evaporated to afford a solid. Filtration using hot hexane gave 1-(bithien-2-yl)-4-nitrobenzene which was recrystallized from benzene/ethanol (1:1), 6.69 g, yield=58%, mp=186–189° C. IR (KBr; cm$^{-1}$) 3099, 1588, 1512, 1338, 1288, 1110 and 849. $^1$H NMR (CDCl$_3$; δ in ppm): 7.062 (dd, J=5.7 and 4.2 Hz, 1H), 7.207 (d, J=4.5 Hz, 1H), 7.268 (m, 2H), 7.398 (d, J=4.5 Hz, 1H), 7.718 (d, J=9.9 Hz, 2H) and 8.242 (d, J=9.9 Hz, 2H). $^{13}$C NMR (CDCl$_3$; δ in ppm): 124.46, 124.61, 124.89, 124.98, 125.35, 125.56, 126.45, 128.06, 136.56, 139.81, 140.18 and 146.46. MS(EI) m/z (rel int): ): 287 [(M)$^+$, 100%], 257 [(M$^+$—NO), 21%], 241 [(M$^+$—NO$_2$), 29%], 229 [(M$^+$—CNO$_2$), 10%] and 208 [(M$^+$—HNO$_2$S), 30%]. Anal. Calcd for C$_{14}$H$_9$NO$_2$S$_2$: C, 58.52; H, 3.16; N, 4.87; S, 22.32. Found: C, 58.85; H, 2.91; N, 4.64; S, 20.95.

EXAMPLE 9

1-(Bithien-2-yl)-4-aminobenzene

A solution of 1-(bithien-2-yl)-4-aminobenzene (1.3 g, 4.52 mmol) in 95% ethanol (80 mL) containing platinum on sulfide carbon (75 mg) was added hydrazine hydrate (1.5 mL). The mixture was refluxed for 15 hours. After cooling, the mixture was filtered and the solvent was evaporated to give a solid. Addition of hexane followed by filtration gave 1-(bithien-2-yl)-4-aminobenzene, recrystallized from chloroform containing 15% hexane, 0.91 g, yield=79%, mp=132.5–134° C. IR (KBr, cm$^{-1}$) 3411, 3329, 3066, 1619, 1498, 1274, 1184, 837 and 798. $^1$H NMR (CDCl$_3$; δ in ppm): 3.740 (br, s, 2H), 6.680 (d, J=9.6 Hz, 2H), 7.005 (dd, J=5.7 and 4.2 Hz, 1H), 7.048 (d, J=4.2 Hz, 1H), 7.094 (d, J=4.2 Hz, 1H), 7.166 (m, 2H) and 7.399 (d, J=9.6 Hz, 2H). $^{13}$C NMR (CDCl$_3$; δ in ppm): 115.28, 121.75, 123.14, 123.89, 124.52, 124.72, 127.20, 127.95, 134.83, 137.77, 143.87 and 146.12. MS(EI) m/z (rel int): 257 [(M)$^+$, 100%], 212 [(M$^+$—HCS), 9%] and 77 [(M$^+$—C$_8$H$_6$NS$_2$), 15%]. Anal. Calcd for C$_{14}$H$_{11}$NS$_2$: C, 65.34; H, 4.31; N, 5.44. Found: C, 65.12; H, 4.21; N, 4.60.

EXAMPLE 10

1-(3,4-didecyloxythien-2-yl)-4-nitrobenzene

To a refluxing solution of 1-bromo-4-nitrobenzene (0.80 g, 3.98 mmol) in toluene (200 mL) was added tetrakis(triphenylphosphine)palladium(0) (75 mg). After 20 min, 2-(tributylstannyl)-3,4-didecyloxythiophene (2.87 g, 4.19 mmol) was added via a syringe. After complete addition, the mixture was refluxed for a total of 15 h. After cooling, the mixture was filtered and evaporated to afford a solid. Filtration using hot hexane gave 1-(3,4-didecyloxy)thien-2-yl)-4-nitrobenzene, recrystallized from ethanol containing 2% acetone, 1.17 g, yield=57%, mp=40–41.5° C. IR (KBr) 3127, 2919, 1594, 1512, 1464, 1339 and 848. $^1$H NMR (δ ppm): 0.880 (t, J=7.2 Hz, 6H), 1.411 (m, 28H), 1.769 (m, 4H), 3.986 (t, J=7.2 Hz, 2H), 4.092 (t, J=7.2 Hz, 2H), 6.263 (s, 1H), 7.903 (d, J=10.2 Hz, 2H) and 8.208 (d, J=10.2 Hz, 2H). $^{13}$C NMR (δ ppm): 14.26, 22.69, 29.34, 29.60, 30.12, 30.64, 30.73, 31.71, 31.91, 32.37, 70.18, 73.09, 97.19, 122.46, 123.94, 126.94, 140.16, 145.08, 145.94 and 150.98. MS(EI) m/z (rel int): 517 [(M)$^+$, 42], 377 [(M$^+$—C$_{10}$H$_{20}$), 18], 359 [(M$^+$—C$_{10}$H$_{22}$O),5], 333 [(M$^+$—C$_{11}$H$_{20}$S), 3],237 [(M$^+$—C$_{20}$H$_{40}$), 55] and 190 [(M$^+$—C$_{20}$H$_{41}$NO$_2$), 8]. Anal. Calcd for C$_{30}$H$_{47}$NO$_4$S: C, 69.59; H, 9.15; N, 2.71; S, 6.19. Found: C, 69.61; H, 9.20; N, 2.63; S, 6.06.

EXAMPLE 11

1-(3,4-didecyloxythien-2-yl)-4-aminobenzene

A solution of 1-(3,4-didecyloxythien-2-yl)-4-nitrobenzene (0.995 g, 1.92 mmol) in 95% ethanol (30 mL)

containing platinum on sulfide carbon (30 mg) was added hydrazine hydrate (0.5 mL). The mixture was refluxed for 5 to 10 hours. After cooling, the mixture was filtered and the solvent was evaporated to give a solid. Addition of hexane followed by filtration gave 1-(3,4-didecyloxythien-2-yl)-4-aminobenzene which was subsequently recrystallized from ethanol containing few drops of acetone, 0.855 g. yield=91%, mp=64.5–65.5° C. IR (KBr; cm$^{-1}$) 3427, 3335, 3116, 2920, 2850, 1624, 1520, 1467, 1372, 1144 and 826. $^1$H NMR (CDCl$_3$; δ in ppm): 0.880 (t, J=7.4 Hz, 6H), 1.381 (m, 28H), 1.700 (m, 4H), 3.947 (m, 4H), 5.992 (s, 1H), 6.674 (d, J=9.5 Hz, 2H) and 7.522 (d, J=9.5 Hz, 2H). $^{13}$C NMR (CDCl$_3$; δ in ppm): 14.11, 22.69, 25.98, 26.12, 29.17, 29.34, 29.60, 30.09, 30.24, 32.05, 69.75, 72.77, 92.47, 114.96, 123.97, 125.96, 128.06, 141.57, 145.45 and 150.75. MS(EI) m/z (rel int): 487 [(M)$^+$, 40%], 346 [(M$^+$—C$_{10}$H$_{21}$), 8.4%], 207 [(M$^+$—C$_{20}$H$_{40}$), 11%], 178 [(M$^+$—C$_{21}$H$_{41}$O), 8.4%], 150 [(M$^+$—C$_{22}$H$_{41}$O$_2$), 7%] and 136 [(M$^+$—C$_{23}$H$_{45}$NO), 11%]. Anal. Calcd for C$_{30}$H$_{49}$NSO$_2$: C, 73.87; H, 10.13; N, 2.87; S, 6.57. Found: C, 73.99; H, 10.66; N, 2.41; S, 6.32.

The monomers of this invention are useful in the fabrication of electrochromic and electrically conducting materials. The thin polymer films resulting from electropolymerization of these monomers are useful as electrochromic materials in electronic display devices, electrochromic windows and devices which require changes in color and degree of light transmittance.

Various modifications may be made to the invention as described without departing from the spirit of the invention or the scope of the appended claims.

We claim:
1. 1-(3,4-Ethylenedioxythien-2-yl)-4-aminobenzene.
2. 1-(Bithien-2-yl)-4-aminobenzene.
3. 1-(3,4-didecyloxythien-2-yl)-4-aminobenzene.

* * * * *